United States Patent
Oeffner

(10) Patent No.: US 8,388,694 B2
(45) Date of Patent: Mar. 5, 2013

(54) HANDLING DEVICE FOR PERSONS WITH A LIMITED GRIPPING FUNCTION AND ALSO WHEELCHAIR COMPRISING A DEVICE OF THIS TYPE

(76) Inventor: Patrick Oeffner, Freiensteinau (DE)

( * ) Notice: Subject to any disclaimer, the term of this patent is extended or adjusted under 35 U.S.C. 154(b) by 1064 days.

(21) Appl. No.: 12/095,285

(22) PCT Filed: Nov. 28, 2006

(86) PCT No.: PCT/DE2006/002105
§ 371 (c)(1),
(2), (4) Date: May 28, 2008

(87) PCT Pub. No.: WO2007/059766
PCT Pub. Date: May 31, 2007

(65) Prior Publication Data
US 2008/0290629 A1   Nov. 27, 2008

(30) Foreign Application Priority Data
Nov. 28, 2005 (DE) .......................... 10 2005 056 874

(51) Int. Cl.
*A61F 2/54* (2006.01)
*A61H 1/00* (2006.01)
(52) U.S. Cl. ................. 623/65; 623/64; 601/5
(58) Field of Classification Search .............. 623/64,
623/65; 601/5, 148, 149, 150, 151, 152;
294/209, 210; 414/9
See application file for complete search history.

(56) References Cited

U.S. PATENT DOCUMENTS

| | | | | | |
|---|---|---|---|---|---|
| 2,545,947 | A | * | 3/1951 | Felip et al. | 623/26 |
| 3,769,636 | A | * | 11/1973 | Friedman | 623/24 |
| 3,942,194 | A | * | 3/1976 | Winter | 623/65 |
| 3,967,321 | A | | 7/1976 | Ryan et al. | |
| 4,711,482 | A | | 12/1987 | Brown et al. | |
| 4,808,187 | A | * | 2/1989 | Patterson et al. | 623/25 |
| 5,329,941 | A | * | 7/1994 | Bodine, Jr. | 602/21 |
| 5,800,561 | A | * | 9/1998 | Rodriguez | 623/26 |
| 6,146,341 | A | * | 11/2000 | Sato et al. | 601/23 |
| 6,660,043 | B2 | * | 12/2003 | Kajitani et al. | 623/64 |
| 6,666,127 | B2 | * | 12/2003 | Peles | 92/50 |
| 6,846,331 | B2 | * | 1/2005 | Senoir | 623/57 |
| 7,537,577 | B2 | * | 5/2009 | Phelan et al. | 602/21 |
| 7,918,808 | B2 | * | 4/2011 | Simmons | 600/590 |
| 2003/0033023 | A1 | * | 2/2003 | McCrae | 623/65 |
| 2004/0106881 | A1 | * | 6/2004 | McBean et al. | 601/5 |

FOREIGN PATENT DOCUMENTS

| | | |
|---|---|---|
| DE | 19536119 | 2/1997 |
| DE | 19700782 | 4/1998 |
| DE | 69916040 | 3/2005 |
| WO | 99/03432 | 1/1999 |

* cited by examiner

Primary Examiner — J. Allen Shriver, II
Assistant Examiner — James M Dolak
(74) Attorney, Agent, or Firm — The Webb Law Firm

(57) ABSTRACT

A handling device for persons with a limited gripping function, in particular for gripping utensils such as pens, comprising an orthotic support adapted to be secured to a part of the body of the person; a utensil holder situated on the support, wherein the utensil holder includes gripping means; and a pneumatic, electric, or magnetic drive system or a combination thereof operative on the gripping means. Also described is a wheelchair, comprising the aforementioned handling device, thus allowing optimum carrying and operation or use of the device.

15 Claims, 2 Drawing Sheets

HANDLING DEVICE FOR PERSONS WITH A LIMITED GRIPPING FUNCTION AND ALSO WHEELCHAIR COMPRISING A DEVICE OF THIS TYPE

BACKGROUND OF THE INVENTION

1. Field of the Invention

The invention relates to a handling device for persons with a limited gripping function, in particular for gripping everyday items or utensils, such as pens.

2. Description of Related Art

Disabled persons who have sufficient motor capacities to move their limbs (arms, although the legs would of course also be conceivable) with a certain degree of control are however frequently prevented by their disabilities from handling items (for example from holding such items in their hands), i.e. for example from gripping and using various everyday items or utensils such as cups, pens, tools or the like in order to write, paint or work therewith. Such persons are generally unable to grip a cup and put it down again and must therefore rely on a straw or on extraneous assistance when drinking. They also need to be able to use or change their tool for themselves when painting, drawing or working. They required the help of others every time they wanted to pick up a different pen or brush. The change-over is then also relatively time-consuming in each case and an assistant must be close at hand at all times.

A broad range of efforts have been made (and are still being made) to improve this situation. There have thus been various attempts to develop rehabilitation robots which might assist or support the everyday lives of those suffering from the most serious disabilities. However, a drawback of these attempts is still their high costs and the complexity of the technical implementation thereof. They are also aimed at a different target group, namely persons whose disability completely prevents them from moving or from controlling automatic aids for themselves.

Also known are so-called gripping aids or reachers which are an aid enabling people who have difficulty walking to pick up or to put down remote items, such as may be found by typing "gripping aid" into Internet search engines or are known from U.S. Pat. No. 4,711,482 A. These are not suitable or not expedient for the aforementioned group of persons either.

In addition, prosthetics has developed highly complex and expensive means which act as a substitute for the hands. All of these means attach great importance to maximum visual adaptation (aesthetics) to the human body, although this is also correspondingly complex and expensive and indeed beyond the means of many.

The rehabilitation of persons suffering from multiple physical disabilities (for example tetraplegics) also frequently involves the production of individual adaptors (orthotics) for the hands to allow such persons to hold for example cutlery, writing or painting means or table tennis bats. Many of these aids also require an assistant for picking up or changing everyday items or utensils.

On the other hand, there are simpler, relatively cost-effective aids allowing users with disabilities to carry out everyday activities such as, for example, writing. Various writing aids or writing orthotics are thus known, as may be seen from the website www.proaktivo.de/produkts_id/2153.html which shows a writing orthotic in which a ring support for the index finger and a pen mount are provided on a hand adaptor (clasp). See also DE 699 16 040 T2, DE 89 07 363 U1, DE 69716 948 T21 DE 200 10 999 U1, DE 197 00 782 A1, DE 195 36 119 C1, DE 88 01 706 U1 or DE 297 05 842 U1. However, these aids do not allow the tool fastened therein to be changed without extraneous assistance either. In addition, a user of these products must also have certain motor capacities in order to be able to use them satisfactorily for his needs.

SUMMARY OF THE INVENTION

The object of the invention is thus to disclose a device of the above-mentioned type that is relatively inexpensive and simple and also safe in design and handling and that allows persons who have a limited gripping function but sufficient other motor capacities to move their limbs (arms and/or legs) at least with some degree of control, to grip for themselves and/or simply and rapidly to change the everyday items, tools or utensils used in their activities.

A further object is to disclose a wheelchair which comprises a device of this type and allows the disabled occupant of the chair to actuate and use the device for himself.

This object is achieved by a device of the above-mentioned type having the features of claim 1 and also by a wheelchair having the features of claim 19. Advantageous embodiments are characterised in the corresponding dependent sub-claims.

Accordingly, at least one adaptor (support) is provided, i.e. a clasp adapted for example for at least one hand and/or a foot or one different part of the body. However, two or more adaptors may also be provided, i.e. for example for both hands or for one hand and one foot, obviously depending on the mobility of the person using the device.

A tool, for example a gripper, preferably a small gripper, with which a pneumatic, electric or magnetic operating system or a combination of systems of this type is associated, is also provided as the utensil holder on the adaptor.

Obviously, according to the invention, a hydraulic operating system may also be provided, as long as this is compatible with the intended low costs of this device.

This allows persons who have the indicated disability, and thus have sufficient motor functions to move an automatic gripping/holding device with the everyday item or utensil fixed therein or a tool, to grip or to hold items for themselves (in the manner of a hand or finger set), in particular in everyday life. The device also allows the user to use commercially available handling tools. Obviously, the user's individual needs must be taken into account in this regard.

It is advantageous if the small gripper provided is a pneumatic, single-acting mini gripper which, for example, is secured to the adaptor by means of a clip. A conventional commercial mini gripper of this type, which is known per se, may preferably have a gripper opening of approx. 10 mm, a holding force acting on the gripper tip of approx. 15 N and a clamping diameter of approx. 10 mm (see for example the range of products from FIPA GmbH). Correspondingly more powerful mini grippers may be used if required.

Obviously, instead of pneumatic grippers or tools, electric or magnetic grippers or tools may also be used, depending on the available operating system, case, type and location of application and/or the type of disability and remaining mobility.

Thus, the adaptor, i.e. the support, can for example be designed for the hand, i.e. fastenable thereto. It may be manufactured using conventional commercial thermoplastics and also further suitable materials used in orthotics/prosthetics. In its nature, it corresponds to the substantially U-shaped thermoplastic clasp of a conventional commercial writing orthotic (see www.practivo.de). According to the invention, on this adaptor, which is individually produced/adapted for each user, a pneumatically operated, single-acting (although double-acting is also possible) mini gripper (having an operating pressure of 6 bar or higher) is fastened to a utensil holder.

In order to fasten the support, in this case the clasp, to the hand securely, the clasp may also be provided in a simple manner with at least one holding strip which has a hook-and-loop or similar quick-acting fastener and loops securely around the hand.

The holder for the gripper can also be attached to the outer circumference of the clasp in such a way that the gripper comes to lie in the palm of the hand and protrudes therefrom with its active end, in which case active holding support, for example by the fingers, is also possible—depending on the mobility of the user's hand. Obviously, the holder for the gripper can also be attached outside the inside of the hand of the clasp, i.e. in the region of the back of the hand, if there is no satisfactory possibility of accommodating it in the region of the inside of the hand.

The pressure supply for the gripper can in this case be controlled by an electrically switchable solenoid valve which can be operated by means of a standard rocker switch for example. This rocker switch can for example be attached to the armrest of the wheelchair and thus be actuatable, for example, by means of the hand, the elbow or the forearm, in which case it is expedient to allocate the switch of one side in each case to the gripper/tool to be operated by the other hand or on the other side. Thus, for example, if a gripper is arranged on the right hand, the switch should be provided on the left armrest and vice versa. Obviously, the switch can also be arranged in the range of movement of the legs, the head or the shoulders.

Power can be supplied via the disabled person's electrically driven wheelchair (24 V, DC) or the batteries or rechargeable batteries thereof.

A compressed air container (0.75 liter, 16 bar) can be used for supplying pressure, equipped with a pressure indicator and a pressure reducer (gripper operating pressure) which is refilled by means of a trade compressor at an operating pressure of 15 bar. When the volume consumed is minimised, this small reservoir is sufficient for approx. 300 gripping operations. Obviously, it is also possible to use a mini compressor on its own all the time, although the noise which is usually generated by this can be most disturbing.

If an electric version of the gripper is employed, use can be made for example of a small gripper from hobby robotics, which can open and close by means of a worm gear and a geared motor (24 V, DC). The first variant can be controlled using a rotary drive controller without any nut overrun, switching between clockwise and anti-clockwise running by means of a selector switch. Obviously, a large number of variants are conceivable in this case too, especially as the choice of electrically operated grippers and tools is constantly increasing.

A magnetic, in particular an electromagnetic, variant is also possible, especially as the power supply is usually available from an electrically driven wheelchair.

Finally, it should be borne in mind that the pneumatic system does not necessarily require a power supply. This allows the device to be carried in a rucksack or other container as well, i.e. for example by persons who have no difficulty walking but still cannot grip or can only grip inadequately.

Also, many tetraplegics use active wheelchairs which do not have a power supply. In this case, the frame of the chair can for example be designed in such a way that it serves as a compressed air reservoir.

In order to make it easier for the user of the device to change utensils, for example pens, the pens can be provided in such a way that they can be grasped easily and securely by the gripper. If these are simply lying on a flat surface, for example a table, then grasping thereof—even from the hand position—is difficult. A cup could also be selected or adapted in such a way as to ensure that it can be picked up, held and put down safely.

It is therefore particularly advantageous if a receiving means is provided in which the pens are held in an easily graspable position and orientation and can be inserted therein and detached therefrom.

Thus for this purpose, for example, an insertion board can be provided having holes formed in its surface with a depth, width and distances from one another, which allow secure insertion and detachment and intermediate gripping. The holes may in this case be formed in such a way that the pens are positioned in a straight row, a zigzag row, in a plurality of rows in succession, parallel or at an angle to one another.

The insertion board can in this case be a flat board or be provided with an upper curvature. It can however overall be shaped in the manner of a cylinder in which the holes are formed radially, forming in the broadest sense a multiple-hole receptacle from which the pens then fan out and can be grasped easily.

In addition, the insertion board, which can be made of wood, plastics material, metal or any suitable material or combination of materials, can be allocated to the device in such a way that the utensils inserted therein can be optimally gripped at all times. Thus, the insertion board can be fastened or fastenable to the wheelchair by means of a holding arm, for example extending at the front next to the armrest, preferably so as to be adjustable in its angular position.

The particular advantages of the device according to the invention may be seen in particular in.
  low costs (all of the components are commercially available);
  low weight—above all the adaptor placed on the hand can be designed to weigh less than 100 grams, even less than 50 grams;
  operation is possible without force;
  high mobility: the system as a whole or the device as a whole can be transported without difficulty, for example can be fastened to the electrically driven wheelchair and is thus portable at all times;
  individual customisation is easily possible, i.e. there is sufficient latitude for adaptation to individual requirements, in particular for operation, installation at the workplace, fastening to the wheelchair, rucksack, adaptor for adapting the tool or tools to the body; there are thus a variety of possibilities for implementing a variety of variants.

In addition, a large number of variants are conceivable in application, with corresponding advantages:
  operation can thus be achieved with all of the switching aids which the auxiliary supply provides (rocker switch with a large rocker arm, proximity switch, blow switch, large keypads, voice recognition);
  there are also various possibilities for the pressure supply, as in this case consideration can be given to individual conditions, from the high-pressure bottle to the mini compressor. A plurality of grippers can also easily be operated at the same time in parallel (for example for both hands);
  the adaptors for the hands or other parts of the body are generally adapted for the user, even if they are standard products. In this case too, orthopaedic mechanics offers numerous possibilities;

the tools to be used can be selected in accordance with the user's requirements and possibilities.

BRIEF DESCRIPTION OF THE DRAWINGS

The invention will be described hereinafter in greater detail based on exemplary embodiments and with reference to the drawings, in which.

DETAILED DESCRIPTION OF THE INVENTION

Figure 1:
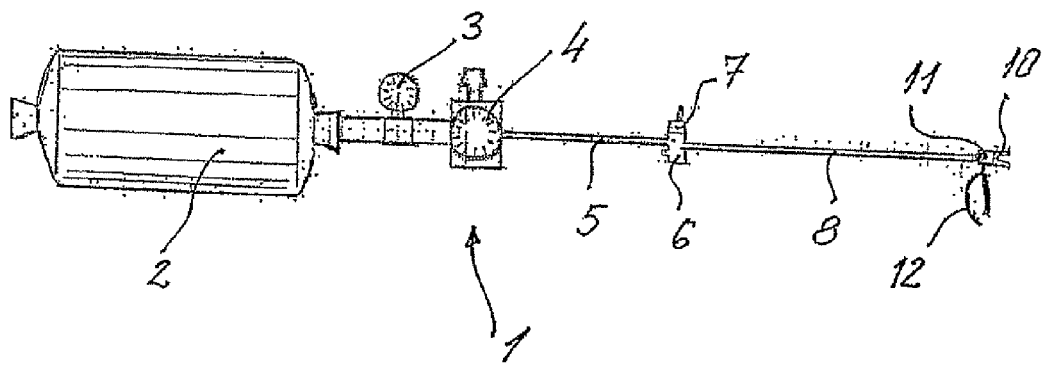
FIG. 1 is a schematic view.

FIG. 1 shows that the device 1 according to the invention is composed substantially of a portable pressure reservoir 2 with which a pressure meter 3 and a pressure reducer 4 are associated. The pressure reducer 4 is connected via a flexible compressed air hose 5 to a solenoid valve 6, for example a 3/2-way valve, which is, for its part, equipped with a switch 7, for example a rocker switch, by means of which it can be switched. From the solenoid valve 6, a flexible pressure hose 8 leads to a pneumatic gripper 10 which, for its part, secures the gripper by means of a utensil holder 11, configured for example in the manner of a cable clip, to an adaptor 12 which is, in turn, configured as a U-shaped clasp and thermoplastically adapted to the shape of a hand for example. A compressor 35, shown in FIG. 5, supplies the compressed air.

Figure 2:
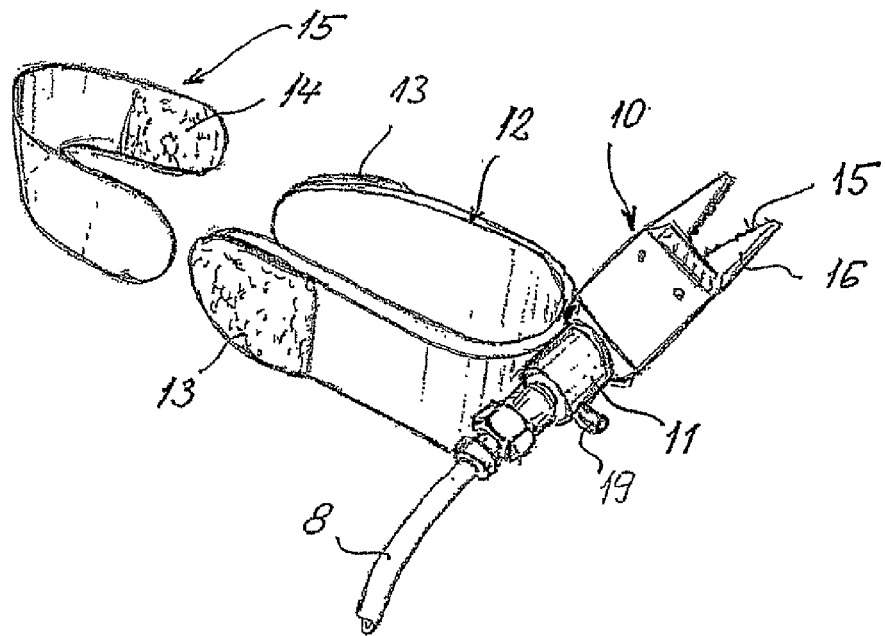
FIG. 2 is a perspective view of a hand-adaptor with a mini gripper fastened thereto and a hook-and-loop holding strip.

FIG. 2 shows more clearly how the substantially U-shaped adaptor-clasp is configured so as to be substantially smooth on its inner surfaces, whereas parts 13 of a hook-and-loop fastener part 13, 14 are attached to the outer leg ends. These hook-and-loop fastener parts 13 co-operate with corresponding hook-and-loop fastener parts 14 provided on the inside at the two ends of a holding strip 15. In this case, the length of the holding strip 15 is designed in such a way that when the support 12 is placed on the hand, the user's metacarpus is securely and safely closed. The cylindrical holder 11, in which the gripper 10 is secured by means of a fixing screw 15, is fastened to the outer surface, facing the opening in the support 12, of the support. The gripper 10 is connected to the pressure hose 8 by means of the connection part 16. In this case, the gripper 10 has two gripper jaws 16 which are ribbed on their straight gripper surfaces 17 to improve gripability. The grip of the gripper jaws 16 can however also be made more secure by corresponding and secure coating of the gripping surfaces 17 or all of the gripper jaws or by longitudinally drawing protective rubber finger stalls over the gripper jaws as required. In some embodiments, the gripper may include a pneumatic chisel 36, shears 37, or a vacuum gripper 38, as shown in FIG. 5.

Figure 3:
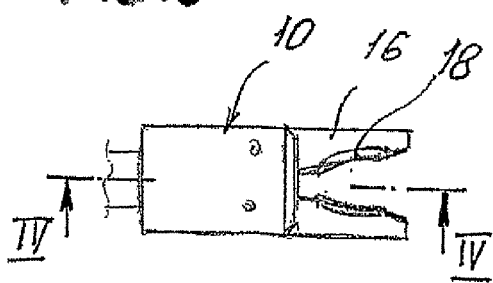
FIG. 3 is a plan view of a gripper with a gripper lining.
Figure 4:
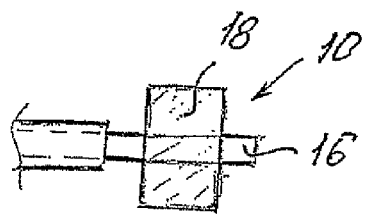
FIG. 4 is a sectional view along the line IV-IV in FIG. 3.

Provided in the grippers 10 shown in FIG. 3 and FIG. 4, in the gripping surfaces of the jaws 16, there is in each case a sheet-like lining 18 which in the longitudinal direction of the gripper has a slightly curved, inward-facing arc shape, thus allowing for example a pen grasped by means of a gripper to be held over a larger circumferential region. In addition, the lining sheets 18 are designed so as to be substantially higher than the jaws 16, preferably at least 1.5× thicker than said jaws, which also makes a substantial contribution to the security of the gripping or holding function.

Figure 5:
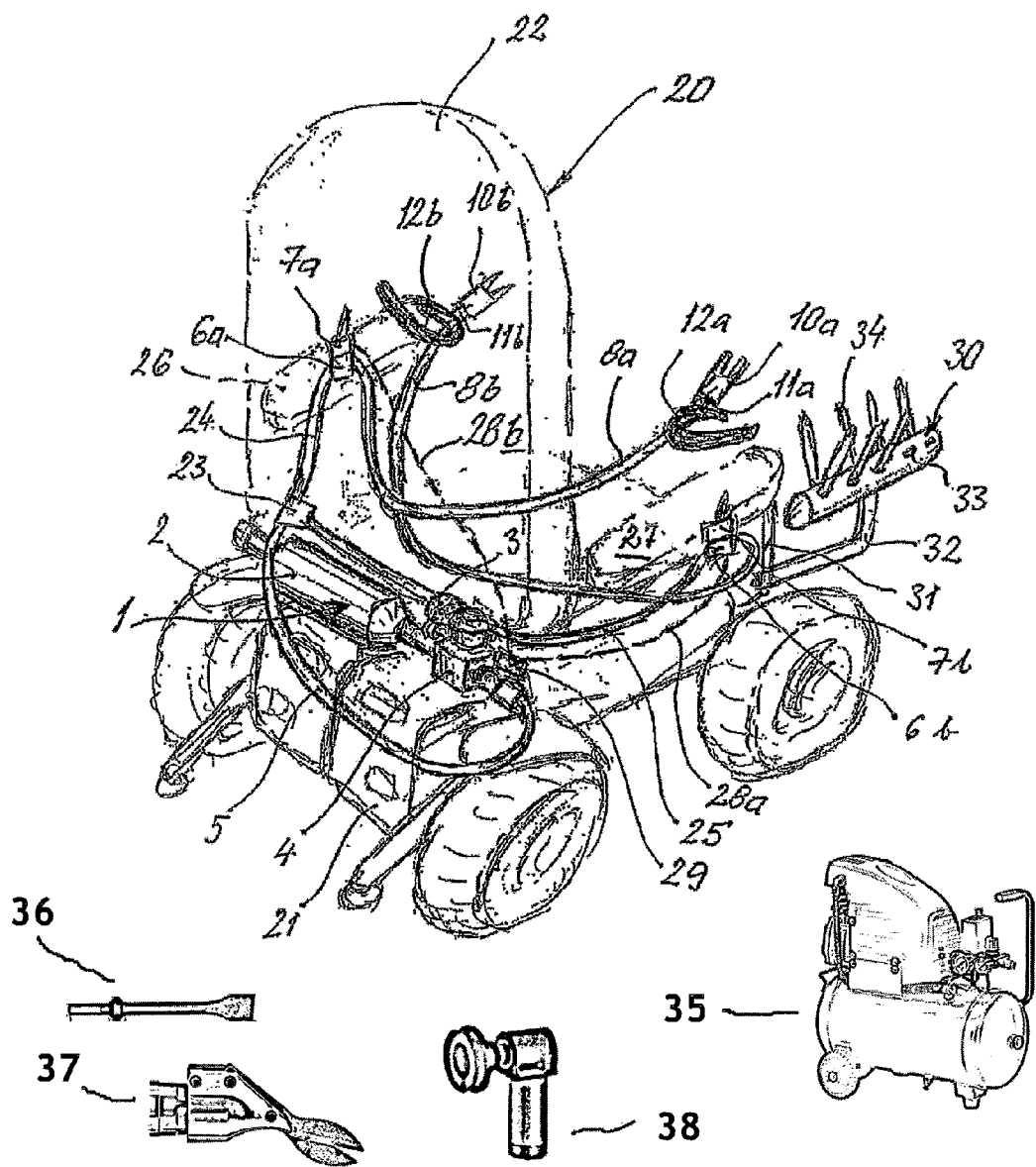
FIG. 5 is a partial perspective view of an electrically driven wheelchair with a device which is attached thereto and has two grippers.

Finally, FIG. 5 shows an electrically driven wheelchair 20 which is equipped with a device 1 according to the invention. In this case, the compressed air reservoir 2 is attached to the back of the wheelchair, just above the upper batteries 21, together with the pressure indicator 3 associated therewith and the pressure reducer 4. From the pressure reducer 4, the flexible pressure hose 5 leads to a distributor 23 on the back of the backrest 22 of the wheelchair, from where, in turn, a respective hose part 24 and a hose part 25 lead to the solenoid valve 6 a which is fastened to the left armrest 26 and has the switch 7 a, and to the solenoid valve 6 b which is fastened to the right armrest 27 and has the switch 7 b. From the solenoid valve 6 a, a hose 8 a leads in turn to the gripper 10 a on the adaptor 12 a, for the right hand, whereas from the right solenoid valve 6 b a pressure hose 8 b leads to the gripper 10 b on the adaptor 12 b for the left hand.

The switches 7 a and 7 b are connected to the terminals of the batteries 21 by means of electric leads 28 a and b.

An in this case cylindrical insertion board 30 is attached to the right armrest 27 and to the corresponding part of the frame 31 by means of a fastening arm 32. The insertion board has radially guided insertion holes 33 in which utensils 34, for example pens can be held in an insertable and detachable manner. It should also be noted that the utensil holder itself and/or the tool received therein can be rotatable in order to increase the number of items which can be reached.

The invention claimed is:

1. A handling device for a person having limited gripping ability for holding and handling utensils, the handling device comprising
   an orthotic support adapted to be secured to a part of the body of the person;
   a utensil holder situated on the support, wherein the utensil holder includes gripping means; and
   a pneumatic, electric, or magnetic drive system or a combination thereof operative on the gripping means by engaging an actuation means,
   wherein operation of the gripping means by engaging the actuation means does not cause corresponding movement of the part of the body of the person to which the orthotic support is secured.

2. The device according to claim 1, wherein the gripping means is a pneumatic single or double-acting gripper, wherein an opening of the gripper is approximately 10 mm, a clamping diameter of the gripper is approximately 10 mm, and a holding force at a tip of the gripper is approximately 15 N.

3. The device according to claim 2, wherein the pneumatic drive system includes a pressure supply having:
   a pressure reservoir that is feedable by a compressor;
   a controller comprising at least one manually or electrically switched solenoid valve and a respective switch for operation thereof; and optionally
   a power supply for powering the switches and compressor.

4. The device according to claim 3, wherein the gripper is constructed to sustain an operating pressure of approximately 6 or 8 bar.

5. The device according to claim 3, wherein the pressure reservoir is sized to contain approximately 0.75 l and approximately 16 bar needed to sustain approximately 300 gripping operations, wherein the pressure reservoir has a diameter of approximately 70 mm and a length of approximately 250 mm.

6. The device according to claim 3, further comprising a pressure reducer for reducing the pressure of the pressure reservoir from 15 bar to an operating pressure of the gripper of approximately 6 or 8 bar, wherein the pressure reducer is situated between the pressure reservoir and the at least one solenoid valve.

7. The device according to claim 1, wherein the gripping means is pivotably adjustable or rotatable on the support, wherein the support is fastened to the gripping means by a cable clip.

8. The device according to claim 3, wherein the switch is a rocker switch, blow switch, large keypad, or a voice recognition switch situated within reach of the person when the support is secured to a part of the body of a person.

9. The device according to claim 1, wherein the electric drive system includes:
- a worm gear and a geared motor for actuating the gripping means between an open and closed position; and
- a rotary drive controller without any nut overrun, configured to switch between clockwise and anti-clockwise motion by a selector switch.

10. The device according to claim 7, wherein the support is constructed of thermoplastic components and one or more hook-and-loop fasteners.

11. The device according to claim 10, wherein the support, when placed on the hand of the person, slides over the thumb and fits around a metacarpus in the form of a U, wherein the one or more hook and loop fasteners are positioned to be looped around the hand, wherein the cable clip of the gripping means is attached to a clasp such that when the support is attached, the gripping means lies substantially in the palm of the hand and protrudes therefrom with gripper jaws of the gripping means.

12. The device according to claim 1, wherein the gripping means includes a pneumatic chisel or shears.

13. The device according to claim 1, wherein the gripping means on at least one gripper jaw thereof, includes ribbings, undulations, coatings, or non-slip jaw linings for providing secure gripping and holding of the utensils held within the gripping means.

14. The device according to claim 13, wherein the one of the ribbings, undulations, coatings, or non-slip jaw linings are directionally adjustable and interchangeable and are constructed of elastic, non-slip material.

15. The device according to claim 1, wherein the gripping means is a vacuum gripper, and wherein the pneumatic drive system produces a vacuum for driving the vacuum gripper.

* * * * *

UNITED STATES PATENT AND TRADEMARK OFFICE
CERTIFICATE OF CORRECTION

PATENT NO. : 8,388,694 B2  Page 1 of 1
APPLICATION NO. : 12/095285
DATED : March 5, 2013
INVENTOR(S) : Patrick Oeffner It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1192 days.

Signed and Sealed this
First Day of September, 2015

Michelle K. Lee
*Director of the United States Patent and Trademark Office*